(12) United States Patent
Jochum et al.

(10) Patent No.: US 6,653,064 B1
(45) Date of Patent: Nov. 25, 2003

(54) METHOD FOR IDENTIFYING COMPOUNDS USEFUL IN THE THERAPY OF BONE DISORDERS

(75) Inventors: Wolfram Jochum, Vienna (AT); Jean-Pierre David, Vienna (AT); Koichi Matsuo, Vienna (AT); Erwin F. Wagner, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 09/668,300

(22) Filed: Sep. 25, 2000

Related U.S. Application Data

(60) Provisional application No. 60/160,022, filed on Oct. 18, 1999.

(30) Foreign Application Priority Data

Sep. 23, 1999 (EP) .............................................. 99118773

(51) Int. Cl.[7] .............................. C12Q 1/00; C12Q 1/68; C12N 15/63; C12N 15/74; C07H 21/04

(52) U.S. Cl. ................................ 435/4; 435/6; 435/7.1; 435/455; 435/320.1; 435/377; 536/23.1; 536/23.2; 536/24.1

(58) Field of Search ................................ 435/6, 4, 325, 435/455, 320.1, 375, 8, 14, 377, 7.1; 800/14, 18, 25, 3; 536/23.1, 23.5, 24.1, 23.2

(56) References Cited

FOREIGN PATENT DOCUMENTS

| WO | WO 91/01379 | 2/1991 |
|---|---|---|
| WO | WO 99/18193 | 4/1999 |

OTHER PUBLICATIONS

Kappel et. al.; Regulating gene expression in transgenic animals, 1992, Current Opinion in Biotechnology 3: 548–553.*

Strojek et. al.; The Use of Trangenic Animal Techniques for Livestock Improvement; 1988, Genetic Engineering: Principles and methods, vol. 10: 221–246.*

Mullins et. al.; Perspectives Series: Molecular Medicine in Genetically Engineered Animals, 1996, J. Clin. Invest. vol. 98, No. 11: S37–S40.*

Hammer et. al.; Genetic Engineering of Mammalian Embryos, 1986, J. Anim. Sci. 63: 269–278.*

Houdebine; Production of pharmaceutical proteins from transgenic animals, 1994, Journal of Biotechnology 34: 269–287.*

Wall; Transgenic Livestock: Progress and Prospects for the Future, 1996, Theriogenology 45: 57–68.*

Miller et.al.; Targeted vectors for gene therapy, 1995, FASEB J. 9: 190–199.*

Verma et.al.; Gene therapy–promises, problems and prospects, 1997, Nature, vol. 389: 238–242.*

Dang et.al.; Gene Therapy and Transltional Cancer Research, 1999, Clinical Cancer Research, vol. 5: 471–474.*

Jochum et al., Increased bone information and osteosclerosis in mice overexpressing the transcription factor Fra–1, 2000, Nature Medicine, vol. 6, pp. 980–984.*

Angel, P. et al., "Phorbol Ester–Inducible Genes Contain a Common Cis Element Recognized by a TPA–Modulated Trans–Acting Factor," *Cell 49:*729–739, Cell Press (1987).

Angel, P. and Karin, M., "the role of Jun, Fos and the AP–1 complex in cell–proliferation and transformation," *Biochim Biophys Acta 1072:*129–157, Elsevier Science BV (1991).

Banerjee, C. et al., "Runt Homology Domain Proteins in Osteoblast Differentiation: AML3/CBFA1 Is a Major Component of a Bone–Specific Complex," *J Cell Biochem 66:* 1–8, Wiley–Liss, Inc. (1997).

Battista, S. et al., "Increase in AP–1 activity is a general event in thyroid cell transformation in vitro and in vivo," *Oncogene 17:*377–385, Stockton Press (1998).

Bauer, D. et al., "Identification of differentially expressed mRNA species by an improved display technique (DDRT––PCR)," *Nucleic Acids Res. 21:*4272–4280, Oxford University Press (1993).

Bergers, G. et al., "Transcriptional Activation of the fra–1 Gene by AP–1 Is Mediated by Regulatory Sequences in the First Intron," *Mol Cell Biol 15:*3748–3758, American Society for Microbiology (1995).

Candeliere, G.A. et al., "Differential Stimulation of Fos and Jun Family Members by Calcitriol in Osteoblastic Cells," *Mol Endocrinol 5:*1780–1788, Williams & Wilkins for The Endocrine Society (1991).

Caricasole, A. and Ward, A., "Transactivation of mouse insulin–like growth factor II (IGF–II) gene promoters by the AP–1 complex," *Nucleic Acids Res 21:*1873–1879, Oxford University Press (1993).

Clohisy, J.C. et al., "Parathyroid Hormone Induces c–fos and c–jun Messengen RNA in Rat Osteoblastic Cells," *Mol Endocrinol 6:*1834–1842, Williams & Wilkins for The Endocrine Society (1992).

(List continued on next page.)

*Primary Examiner*—Remy Yucel
*Assistant Examiner*—Quang Nguyen
(74) *Attorney, Agent, or Firm*—Sterne, Kessler, Goldstein & Fox PLLC

(57) ABSTRACT

The present invention relates to a screening method for identifying a substance for the treatment of bone disorders that are associated with reduced bone mass in which the substance is tested for its ability to upregulate the expression of Fra-1 or to modulate the expression of a Fra-1 target gene in osteoblasts where the upregulation or modulation results in an increased bone formation in vivo. The identified osteoinductive compounds and DNA molecules encoding biologically active Fra-1 molecules can be used for the therapy of bone disorders characterized by a circumscribed or systemic reduction of bone mass.

22 Claims, 7 Drawing Sheets

OTHER PUBLICATIONS

Cohen, D.R. and Curran, T., "fra–1: a Serum–Inducible, Cellular Immediate–Early Gene That Encodes a Fos–Related Antigen," *Mol Cell Biol 8:*2063–2069, American Society for Microbiology (1988).

Cohen, D.R. et al., "The product of a fos–related gene, fra–1, binds cooperatively to the AP–1 site with Jun: transcription factor AP–1 is comprised of multiple protein complexes," *Genes Dev 3:*173–184, Cold Spring Harbor Laboratory Press (1989).

Cohen, D.R. et al., "Transcriptional regulation in the testis: a role for transcription factor AP–1 complexes at various stages of spermatogenesis," *Oncogene 8:*443–455, Macmillan Press Ltd (1993).

DeRisi,J.L. et al., "Exploring the Metabolic and Genetic Control of Gene Expression on a Genomic Scale," *Science 278:*680–686, American Association for the Advancement of Science (1997).

De Wet, J.R. et al., "Firefly Luciferase Gene: Structure and Expression in Mammalian Cells," *Mol Cell Biol 7:*725–737, American Society for Microbiology (1987).

Diatchenko, L. et al., "Suppression subtractive hybridization: A method for generating differentially regulated or tissue–specific cDNA probes and libraries," *Proc Natl Acad Sci USA 93:*6025–6030, National Academy of Sciences of the USA (1996).

Dony, C. and Gruss, P., "Proto–oncogene c–fos expression in growth regions of fetal bone and mesodermal web tissue," *Nature 328:*711–714, Macmillan Publishers Ltd (1987).

Ducy, P. et al., "Increased bone formation in osteocalcin––deficient mice," *Nature 382:*448–452, Macmillan Publishers Ltd (1996).

Ducy, P. et al., "Osf2/Cbfa1: a Transcriptional Activator of Osteoblast Differentiation," *Cell 89:*747–754, Cell Press (1997).

Ducy, P. et al., "A Cbfa1–dependent genetic pathway controls bone formation beyond embryonic development," *Genes Dev 13:*1025–1036, Cold Spring Harbor Laboratory Press (1999).

Filvaroff, E. and Derynck, R., "Bone remodeling: A Signalling system for osteoclast regulation," *Curr Biol 8:*R679–R682, Current Biology Ltd (1998).

Gandarilllas, A. and Watt, F.M., "Changes in expression of members of the fos and jun families amd myc network during terminal differentiation of human keratinocytes," *Oncogene 11:*1403–1407, Stockton Press (1995).

Grigoriadis, A.E. et al., "Osteoblasts are Target Cells for Transformation in c–fos Transgenic Mice," *J Cell Biol 122:*685–701, Rockefeller University Press (1993).

Grigoriadis, A.E. et al., "c–Fos: A Key Regulator of Osteoclast–Macrophage Lineage Determination and Bone Remodeling," *Science 266:*443–448, American Association for the Advancement of Science (1994).

Guo, X. et al., "Identification of a ras–Activated Enhancer in the Mouse Osteopontin Promoter and Its Interaction with a Putative ETS–Related Transcription Factor Whose Activity Correlates with the Metastatic Potential of the Cell," *Mol Cell Biol 15:*476–487, American Socity for Microbiology (1995).

Hou, Z. et al., "Osteoblast–specific gene expression after transplantation of marrow cells: Implications for skeletal gene therapy," *Proc Natl Acad Sci USA 96:*7294–7299, National Academy of Science of the USA (1999).

Hubank, M. and Schatz, D.G., "Identifying differences in mRNA expression by representational difference analysis of cDNA," *Nucleic Acids Res 22:*5640–5648, Oxford University Press (1994).

Huo, L. and Rothstein, T.L., "Isolation and Characterization of Murine fra–1: Induction Mediated by CD40 and Surface Ig Is Protein Kinase C Dependent," *J Immunol 157:*3812–3818, American Association of Immunologists (1996).

Iotsova, V. et al., "Osteopetrosis in mice lacking NF–κB1 and NF–κB2," *Nat Med 3:*1285–1289, Nature America Inc. (1997).

Johnson, R.S. et al., "Pleiotropic Effects of a Null Mutation in the c–fos Proto–Oncogene," *Cell 71:*577–586, Cell Press (1992).

Joyce, M.E. et al., "Transforming Growth Factor–β and the Initiation of Chondrogenesis and Osteogenesis in the Rat Femur," *J Cell Biol 110:*2195–2207, Rockefeller University Press (1990).

Kallunki, T. et al., "JNK2 contains a specificity–determining region responsible for efficient c–Jun binding and phosphorylation," *Genes Dev 8:*2996–3007, Cold Spring Harbor Laboratory Press (1994).

Kim, S.J. et al., "Autoinduction of Transforming Growth Factor β1 Is Mediated by the AP–1 Complex," *Mol Cell Biol 10:*1492–1497, American Society for Microbiology (1990).

Koe, R.C. et al., "Parathyroid Hormone versus Phorbol Ester Stimulation of Activator Protein–1 Gene Family Members in Rat Osteosarcoma Cells," *Calcif Tissue Int 61:*52–58, Springer–Verlag (1997).

Komori, T. et al., "Targeted Disruption of Cbfa1 Results in a Complete Lack of Bone Formation owing to Maturational Arrest of Osteoblasts," *Cell 89:*755–764, Cell Press (1997).

Kong, Y.Y. et al., "OPGL is a key regulator of osteoclastogenesis, lymphocyte development and lymph–node organogenesis," *Nature 397:*315–323, Macmillan Publishers Ltd (1999).

Kratochwil, K. et al., "Retrovirus–Induced Insertional Mutation in Mov13 Mice Affects Collagen I Expression in a Tissue–Specific Manner," *Cell 57:*807–816, Cell Press (1989).

Kustikova, O. et al., "Fra–1 Induces Morphological Transformation and Increases In Vitro Invasiveness and Motility of Epithelioid Adenocarcinoma Cells," *Mol Cell Biol 18:*7095–7105, American Society for Microbiology (1998).

Liang, P. and Pardee, A.B., "Differential Display of Eukaryotic Messenger RNA by Means of the Polymerase Chain Reaction," *Science 257:*967–971, American Association for the Advancement of Science (1992).

Machwate, M. et al., "c–fos Protooncogene Is Involved in the Mitogenic Effect of Transforming Growth Factor–β in Osteoblastic Cells," *Mol Endocrinol 9:*187–198, William & Wilkins for The Endocrine Society (1995).

McCabe, L.R. et al., "Selective Expression of fos– and jun–Related Genes during Osteoblast Proliferation and Differentiation," *Exp Cell Res 218:*255–262, Academic Press Inc. (1995).

McCabe, L.R. et al., "Developmental Expression and Activities of Specific Fos and Jun Proteins Are Functionally Related to Osteoblast Maturation: Role of Fra–2 and Jun D during Differentiation," *Endocrinology 137:*4398–4408, The Endocrine Society (1996).

McHenry, J.Z. et al., "Overexpression of fra–2 in transgenic mice perturbs normal eye development," *Oncogene* 17:1131–1140, Stockton Press (1998).

Mechta, F. et al., "Transformation by ras modifies AP1 composition and activity," *Oncogene* 14:837–847, Stockton Press (1997).

Merz, W.A. and Schenk, R.K., "A quantitative histological study on bone formation in human cancellous bone," *Acta Anat* 76:1–15, S. Karger (1970).

Morello, D. et al., "Studies on the expression of an H–2K/ human growth hormone fusion gene in giant transgenic mice," *EMBO J* 5:1877–1883, Oxford University Press (1986).

Noda, M. and Camilliere, J.J., "In Vivo Stimulation of Bone Formation by Transforming Growth Factor–β," *Endocrinology* 124:2991–2994, The Endocrine Society (1989).

Otto, F. et al., "Cbfa1, a Candidate Gene for Cleidocranial Dysplasia Syndrome, Is Essential for Osteoblast Differentiation and Bone Development," *Cell* 89:765–771, Cell Press (1997).

Owen, T.A. et al., "Coordinate occupancy of AP–1 sites in the vitamin D–responsive and CCAAT box elements by Fos–Jun in the osteocalcin gene: Model for phenotype suppression of transcription," *Proc Natl Acad Sci USA* 87:9990–9994, National Academy of Science of the USA (1990).

Ownes, J.M. et al., "Fra–1 Potentiates Osteoclastic Differentiation in Osteoclast–Macrophage Precursor Cell Lines," *J Cell Physiol* 179:170–178, Wiley–Liss, Inc. (1999).

Parfitt, A.M. et al., "Bone Histomorphometry: Standardization of Nomenclature, Symbols, and Units. Report of the ASBMR Histomorphometry Nomenclature Committee," *J Bone Miner Res* 2:595–610, Mary Ann Liebert, Inc. (1987).

Pasquali, C. et al., "Preparative two–dimensional gel electrophoresis of membrane proteins," *Electrophoresis* 18:2573–2581, Wiley–VCH Verlag GmbH (1997).

Pendas, A.M. et al., "Structural Analysis and Promoter Characterization of the Human Collagenase–3 Gene (MMP13),"0 *Genomics* 40:222–233, Academic Press Inc. (1997).

Pennington, S.R. et al., "Proteome analysis: from protein characterization to biological function," *Trends Cell Biol* 7:168–173, Elsevier Science Ltd (1997).

Ramsay, G., "DNA Chips: State–of–the–art," *Nature Biotechnol* 16:40–44, Nature America Inc. (1998).

Rutberg, S.E. et al., "Differentiation of mouse keratinocytes is accompanied by PKC–dependent changes in AP–1 proteins," *Oncogene* 13:167–176, Stockton Press (1996).

Ruther, U. et al., "c–fos expression induces bone tumors in transgenic mice," *Oncogene* 4:861–865, Macmillan Press Ltd (1989).

Ryseck, R.P. and Bravo, R., "c–JUN, JUN B, and JUN D differ in their binding affinities to AP–1 and CRE consensus sequences: effect of FOS proteins," *Oncogene* 6:533–542, Macmillan Press Ltd (1991).

Saftig, P. et al., "Impaired osteoclastic bone resorption leads to osteopetrosis in cathepsin–K–deficient mice," *Proc Natl Acad Sci USA* 95:13453–13458, National Academy of Science of the USA (1998).

Sandberg, M. et al., "Enhanced expression of TGF–β and c–fos mRNAs in the growth plates of developing human long bones," *Development* 102:461–470, The Company of Biologiests Ltd (1988).

Schena, M. et al., "Quantitative Monitoring of Gene Expression Patterns with a Complementary DNA Microarray," *Science* 270:467–470, American Association for the Advancement of Science (1995).

Schreiber, M. et al., "Structure and chromosomal assignment of the mouse fra–1 gene, and its exclusion as a candidate gene for OC (osteosclerosis)," *Oncogene* 15:1171–1178, Stockton Press (1997).

Schule, R. et al., "Jun–Fos and Receptors for Vitamins A and D Recognize a Common Response Element in the Human Osteocalcin Gene," *Cell* 61:497–504, Cell Press (1990).

Simonet, W.S. et al., "Osteoprotegerin: A Novel Secreted Protein Involved in the Regulation of Bone Density," *Cell* 89:309–319, Cell Press (1997).

Slootweg, M.C. et al., "Growth hormone induces expression of c–jun and jun B oncogenes and employs a protein kinase C signal transduction pathway for the induction orf c–fos oncogene expression," *J Mol Endocrinol* 6:179–188, Journal of Endocrinology Ltd (1991).

Smeyne, R.J. et al., "Temporal and spatial expression of a fos–lacZ transgene in the developing nervous system," *Mol Brain Res* 16:158–162, Elsevier Science Publishers B.V. (1992).

Suzuki, T. et al., "Difference in transcriptional regulatory function between c–Fos and Fra–2," *Nucleic Acids Res* 19:5537–5542, Oxford University Press (1991).

Tondravi, M.M. et al., "Osteopetrosis in mice lacking haematopoietic transcription factor PU.1," *Nature* 386:81–84, Macmillan Publishers Ltd (1997).

Vallone, D. et al., "Neoplastic transformation of rat thyroid cells requires the junB and fra–1 gene induction which is dependent on the HMGI–C gene product," *EMBO J* 16:5310–5321, Oxford University Press (1997).

Wang, Z.Q. et al., "Bone and haematopoietic defects in mice lacking c–fos," *Nature* 360:741–745, Macmillan Publishers Ltd (1992).

Welter, J.F. and Eckert, R.L., "Differential expression of the fos and jun family members c–fos, fosB, Fra–1, Fra–2, c–jun, junB and junD during human epidermal keratinocyte differentiation," *Oncogene* 11:2681–2687, Stockton Press (1995).

Wisdom, R. and Verma, I.M., "Proto–Oncogene FosB: the Amino Terminus Encodes a Regulatory Function Required for Transformation," *Mol Cell Biol* 13:2635–2643, American Society for Microbiology (1993).

Wodicka, L. et al., "Genome–wide expression monitoring in *Saccharomyces cerevisiae.*" *Nature Biotechnol* 15:1359–1367, Nature America Inc. (1997).

Yoshioka, K. et al., "Antitumor promotion by phenolic antioxidants: Inhibition of AP–1 activity through induction of Fra expression," *Proc Natl Acad Sci USA* 92:4972–7976, National Academy of Science of the USA (1995).

* cited by examiner

SEQUENCE LISTING

```
<160> NUMBER OF SEQ ID NOS:    12

<210> SEQ ID NO 1
<211> LENGTH: 21
<212> TYPE: DNA
<213> ORGANISM: synthetic DNA
<220> FEATURE:
<221> NAME/KEY: primer_bind
<222> LOCATION: (1)..(21)
<223> OTHER INFORMATION: synthetic primer

<400> SEQUENCE: 1
cgatcaccaa gaaccaatca g                                              21

<210> SEQ ID NO 2
<211> LENGTH: 22
<212> TYPE: DNA
<213> ORGANISM: synthetic DNA
<220> FEATURE:
<221> NAME/KEY: primer_bind
<222> LOCATION: (1)..(22)
<223> OTHER INFORMATION: synthetic primer

<400> SEQUENCE: 2
gggattaaat gcatgcctag ct                                             22

<210> SEQ ID NO 3
<211> LENGTH: 23
```

```
<212> TYPE: DNA
<213> ORGANISM: synthetic DNA
<220> FEATURE:
<221> NAME/KEY: primer_bind
<222> LOCATION: (1)..(23)
<223> OTHER INFORMATION: synthetic primer

<400> SEQUENCE: 3
gtaccgagac tacggggaac cgg                                           23

<210> SEQ ID NO 4
<211> LENGTH: 24
<212> TYPE: DNA
<213> ORGANISM: synthetic DNA
<220> FEATURE:
<221> NAME/KEY: primer_bind
<222> LOCATION: (1)..(24)
<223> OTHER INFORMATION: synthetic primer

<400> SEQUENCE: 4
tggcttggag tagcaccagc aagg                                          24

<210> SEQ ID NO 5
<211> LENGTH: 23
<212> TYPE: DNA
<213> ORGANISM: synthetic DNA
<220> FEATURE:
<221> NAME/KEY: primer_bind
<222> LOCATION: (1)..(23)
<223> OTHER INFORMATION: synthetic primer

<400> SEQUENCE: 5
gtaccgagac tacggggaac cgg                                           23

<210> SEQ ID NO 6
<211> LENGTH: 25
<212> TYPE: DNA
<213> ORGANISM: synthetic DNA
<220> FEATURE:
<221> NAME/KEY: primer_bind
<222> LOCATION: (1)..(25)
<223> OTHER INFORMATION: synthetic primer

<400> SEQUENCE: 6
ccgctacaga tcctcttctg agatg                                         25

<210> SEQ ID NO 7
<211> LENGTH: 20
<212> TYPE: DNA
<213> ORGANISM: synthetic DNA
<220> FEATURE:
<221> NAME/KEY: primer_bind
<222> LOCATION: (1)..(20)
<223> OTHER INFORMATION: synthetic primer

<400> SEQUENCE: 7
tggaagggat gaaaggctgc                                               20

<210> SEQ ID NO 8
<211> LENGTH: 20
<212> TYPE: DNA
<213> ORGANISM: synthetic DNA
<220> FEATURE:
<221> NAME/KEY: primer_bind
<222> LOCATION: (1)..(20)
<223> OTHER INFORMATION: synthetic primer

<400> SEQUENCE: 8
```

-continued

```
tggacgacac catttgtggc                                          20

<210> SEQ ID NO 9
<211> LENGTH: 24
<212> TYPE: DNA
<213> ORGANISM: synthetic DNA
<220> FEATURE:
<221> NAME/KEY: primer_bind
<222> LOCATION: (1)..(24)
<223> OTHER INFORMATION: synthetic primer

<400> SEQUENCE: 9
gaccatgaga ttggcagtga tttg                                     24

<210> SEQ ID NO 10
<211> LENGTH: 21
<212> TYPE: DNA
<213> ORGANISM: synthetic DNA
<220> FEATURE:
<221> NAME/KEY: primer_bind
<222> LOCATION: (1)..(21)
<223> OTHER INFORMATION: synthetic primer

<400> SEQUENCE: 10
tgatgttcca ggctggcttt g                                        21

<210> SEQ ID NO 11
<211> LENGTH: 24
<212> TYPE: DNA
<213> ORGANISM: synthetic DNA
<220> FEATURE:
<221> NAME/KEY: primer_bind
<222> LOCATION: (1)..(24)
<223> OTHER INFORMATION: synthetic primer

<400> SEQUENCE: 11
aatggtgaga cgtggaaacc cgag                                     24

<210> SEQ ID NO 12
<211> LENGTH: 25
<212> TYPE: DNA
<213> ORGANISM: synthetic DNA
<220> FEATURE:
<221> NAME/KEY: primer_bind
<222> LOCATION: (1)..(25)
<223> OTHER INFORMATION: synthetic primer

<400> SEQUENCE: 12
cgactcctac atcttctgag tttgg                                    25
```

METHOD FOR IDENTIFYING COMPOUNDS USEFUL IN THE THERAPY OF BONE DISORDERS

This application claims the benefit of the filing date of provisional application 60/160,022 filed on Oct. 18, 1999, which is herein incorporated by reference.

The present invention relates to the therapy of bone disorders associated with reduced bone mass.

Bone formation, the synthesis and deposition of extracellular matrix, is essential for skeletal growth, modeling, remodeling and repair. Osteoblasts, the bone-forming cell type of the skeleton, originate from pluripotent mesenchymal stem cells. The differentiation and proliferation of osteoblasts can be modulated by numerous extracellular factors such as hormones, growth factors and cytokines. Recently, the transcription factor Cbfa-1 was found to be essential for osteoblast differentiation (Banerjee, et al., 1997; Ducy, et al., 1997; Otto, et al., 1997; Komori, et al., 1997). However, the molecular mechanisms which control bone formation in vivo are poorly understood.

Activator protein-1 (AP-1) is a dimeric transcription factor composed of Jun, Fos or ATF (activating transcription factor) family members. AP-1 binds to a common DNA site, the AP-1 binding site, and converts extracellular signals into changes in the transcription of many cellular and viral genes (reviewed in Angel and Karin, 1991). AP-1 activity is modulated by various signals including growth factors, cytokines, tumor promoters, carcinogens and specific oncogenes. AP-1 has been implicated in a number of biological processes such as cell proliferation, cell differentiation and apoptosis. However, analysis of AP-1 functions in vivo and in tissue culture cells have shown that different AP-1 members regulate different target genes and thus execute distinct biological functions in a cell-type specific fashion.

Several lines of evidence suggest that AP-1 participates in the control of osteoblast functions. Consensus AP-1 DNA binding sites are present in the promoter regions of genes involved in the regulation of osteoblast growth, differentiation, and extracellular matrix formation and degradation, such as alkaline phosphatase, type I collagen, osteocalcin, osteopontin, and matrix metalloproteases-1 and -13 (Owen, et al., 1990; Schule, et al., 1990; Guo, et al., 1995; Angel, et al., 1987; Pendas, et al., 1997). A number of regulators of osteoblast proliferation and differentiation, including transforming growth factor-$\beta$ (TGF-$\beta$), parathyroid hormone, growth hormone and 1,25-dihydroxyvitamin D, induce the expression of AP-1 components in vitro and in vivo in osteoblastic cells (Candeliere, et al., 1991; Slootweg, et al., 1991; Clohisy, et al., 1992; Machwate, et al., 1995; Koe, et al., 1997). Moreover, the various components of the AP-1 complex are differentially expressed during osteoblast differentiation in vitro and can be detected at sites of active bone formation in vivo (Dony and Gruss, 1987; Sandberg, et al., 1988; Smeyne, et al., 1992; McCabe, et al., 1995; McCabe, et al., 1996).

Fra-1 is an immediate early gene encoding one member of the AP-1 family of transcription factors which shows extensive amino acid homology to c-Fos (Cohen and Curran, 1988). Fra-1 forms heterodimeric complexes with all Jun proteins (c-Jun, junB, junD) and interacts with AP-1 binding sites to regulate gene transcription (Cohen, et al., 1989; Ryseck and Bravo, 1991; Suzuki, et al., 1991). Unlike c-Fos, Fra-1 lacks a C-terminal transactivation domain (Wisdom and Verma, 1993). In addition to induction by serum and mitogens, Fra-1 expression is regulated upon lymphocyte activation and during the differentiation of keratinocytes, spermatocytes and osteoblasts (McCabe, et al., 1995; McCabe, et al., 1996; Cohen and Curran, 1988; Cohen, et al., 1993; Welter and Eckert, 1995; Gandarillas and Watt, 1995; Huo and Rothstein, 1996; Rutberg, et al., 1996). Moreover, ectopic expression of Fra-1 in osteoclast progenitor cell lines potentiates osteoclast development (Owens, et al., 1999).

Reduced bone mass, either circumscribed or systemic, results in impaired bone strength and predisposes to pathological fractures.

Common causes of localized osteolytic lesions are metastatic bone disease, multiple myeloma and lymphoma. In addition, circumscribed bone defects can be caused by numerous benign bone disorders including, among others, bone cysts, fibrous dyslasia, infections, benign bone tumors and impaired fracture healing. Current treatment of these lesions comprises surgical removal or radiotherapeutic destruction of the pathological tissue, fracture fixation, implant stabilization and the reconstruction of the skeletal defect. However, current surgical methods utilizing autograft or allograft bone to close the skeletal defects have limitations. Autograft procedures can result in donor site fracture and donor-site pain, and are limited by the amount of autogenous bone available. Allograft is biologically inactive in the host and has immunological and infectious disease risks.

In contrast, osteoporosis is a systemic disease characterized by low bone mass and microarchitectural deterioration in the entire skeleton with a consequent increase in bone fragility and susceptibility to fracture, especially of bones subjected to major mechanical forces.

Bone is remodeled throughout life, involving the coordinate occurence of bone resorption and bone formation. Osteoporosis develops if the rate of bone resorption exceeds the rate of bone formation resulting in a progressive loss of bone mass. A large number of risk factors for osteoporosis have been identified including aging and loss of gonadal function. In addition, osteoporosis is associated with various endocrine, haematologic, gastrointestinal and rheumatologic diseases, and can be the consequence of therapy with glucocorticoids, heparin, and antiepileptic drugs. The major clinical manifestation of osteoporosis are vertebral body fractures, leading to pain in the back and deformity of the spine. The diagnosis of osteoporosis is based on reduced bone mass, usually assessed by measuring bone mineral density. Most of the drugs used to treat osteoporosis act by decreasing bone resorption, including estrogens, bisphosphonates, and calcitonin. Therapeutic regimens which effectively stimulate bone formation are not available. Although sodium fluoride therapy results in large increases in bone mineral density, its effect on fracture rates is small, since it stimulates the formation of a bone matrix with low mechanical strength.

It was the object of the present invention to provide an improved therapy to restore the mechanical properties of affected bone(s) by enhancing bone formation, either locally or in the entire skeleton, in individuals suffering from bone disorders that are associated with a circumscribed or systemic reduction of bone tissue.

In order to provide a therapeutic approach based on the administration of drugs that are capable of stimulating bone formation, the cellular and molecular mechanisms underlying bone formation were studied.

In order to study the consequences of ectopic Fra-1 expression in vivo, transgenic mice were generated which express high levels of Fra-1 in a broad range of tissues, including bone. It was shown that ectopic Fra-1 expression stimulates bone formation by osteoblasts leading to the development of increased bone mass in the entire skeleton. Furthermore, the data obtained in the experiments of the present invention indicate that constitutive Fra-1 expression promotes osteoblast proliferation and differentiation, since transgenic bones contain increased numbers of mature osteoblasts. Moreover, osteoblastic cells derived from transgenic mice were shown to undergo an accelerated course of differentiation in vitro indicating that Fra-1 can positively regulate bone formation in vivo and in vitro.

Maintenance of bone mass depends on the balance between bone formation by osteoblasts and bone resorption by osteoclasts. In the majority of mouse models of increased bone mass reported on to date, impairment of bone resorption is causal, due to defects either in osteoclast differentiation or function, resulting in osteopetrosis (Johnson, et al., 1992; Wang, et al., 1992; Grigoriadis, et al., 1994; Iotsova, et al., 1997; Simonet, et al., 1997; Tondravi, et al., 1997; Saftig, et al., 1998; Kong, et al., 1999). In contrast, the mouse model of the present invention, i.e. fra-1 transgenic mice, were shown to develop increased bone mass as a consequence of increased bone formation by promoted osteoblast differentiation, rather than decreased bone resorption by osteoclasts. Several lines of evidence support this conclusion. Histomorphometric parameters measuring bone formation were increased in the fra-1 transgenic mice. Grafting experiments revealed that the cause of the bone phenotype resides in transgenic osteoblasts and is therefore not due to secondary effects, e.g. increased hormone secretion: chimeric bones formed by transgenic osteoblasts and wild-type osteoclasts develop increased bone formation, whereas bones composed of wild-type osteoblasts and transgenic osteoclasts display no histological features of increased bone mass. Indirect evidence is provided by the observations that osteoclasts are present in transgenic mice and cover bone surfaces to an comparable extent in transgenic and wild-type mice. Finally, transgenic osteoclasts resorb bone matrix in vitro indicating that reduced resorption function is not the cause for increased bone mass in transgenic skeletons.

To date, the regulation of bone formation by transcription factors has been poorly understood at the molecular level. Beyond its essential function during embryonic development, Cbfa-1 also controls the deposition of bone extracelluar matrix in adult mice (Ducy, et al., 1999). In contrast to Cbfa-1, which regulates the synthesis of extracellular matrix at the level of the single osteoblast, Fra-1 appears to increase the number of active osteoblasts as indicated by increased histomorphometric values for osteoblast surface and mineralizing surface. In contrast, mineral apposition rate and osteoid thickness were comparable in transgenic and wild-type femora, suggesting that the bone forming activity of transgenic osteoblasts is largely unchanged.

Under differentiating conditions in vitro, osteoblastic cells undergo a defined pattern of differentiation characterized by the temporal expression of osteoblast-specific genes. It could be shown by the present inventors that cultures of the transgenic osteoblasts display an accelerated time course of ALP activity and mineralization indicating that Fra-1 expression promotes the differentiation of progenitor cells into bone-forming osteoblasts. The molecular mechanism by which Fra-1 enhances osteoblast differentiation is unknown. Without wishing to be bound by theory, Fra-1 could induce the expression of growth factor receptors or growth factors in osteoblasts. Candidate factors are TGF-$\beta$1 and the insulin-like growth factor-2, both positive regulators of bone formation in vitro and in vivo, which are considered to be potential AP-1 target genes, since the expression of both genes is inducible by AP-1 (Noda and Camilliere, 1989; Joyce, et al., 1990; Kim, et al., 1990; Caricasole and Ward, 1993). Mice carrying a targeted disruption of the osteocalcin gene show a similar, although milder, bone phenotype raising the possibility that Fra-1 may act by decreasing osteocalcin expression in transgenic osteoblasts (Ducy, et al., 1996). However, osteocalcin expression was slightly increased in the calvariae of transgenic and wild-type mice suggesting that Fra-1 acts independently of osteocalcin. Alternatively, Fra-1 could directly induce positive regulators of the cell cycle leading to increased proliferation within the osteoblast lineage. Interestingly, Fra-1 together with c-Jun are able to upregulate cyclin D1 expression in fibroblasts (Mechta, et al., 1997).

It was shown that osteoblasts display a high susceptibilty to elevated levels of Fra-1 expression. The stimulatory effect on bone formation appears to be specific for Fra-1 in comparison to other members of the AP-1 family of transcription factors. Mice expressing high levels of FosB, Fra-2, c-Jun or JunB in bone tissue show no skeletal phenotype (Grigoriadis, et al., 1993; McHenry, et al., 1998). However, c-Fos, another member of the Fos subfamily of AP-1 factors, displays a similar tropism for the osteoblast lineage. Overexpression of c-Fos in transgenic mice results in osteoblast transformation and the development of skeletal osteosarcomas (Grigoriadis, et al., 1993; Ruther, et al., 1989)

Thus, the finding of the present invention that Fra-1 is a positive regulator of bone formation, provides the basis for using Fra-1 as a target for pharmaceutical intervention in pathological conditions in which bone mass is reduced or bone formation is impaired, e.g. in osteoporosis or impaired fracture healing.

The findings of the present invention can be harnessed for designing assays for identifying compounds that upregulate Fra-1 expression and thus are osteoinductive drug candidates for the treatment of bone disorders.

The present invention is directed to a method for identifying a substance for the treatment of bone disorders associated with reduced bone mass, characterized in that the substance is tested for its ability to modulate the expression of Fra-1 or a Fra-1 target gene in osteoblasts, said upregulation or modulation resulting in an increase of bone mass in vivo.

In a first aspect, the substances are tested for their ability to upregulate the expression of Fra-1.

In an embodiment of the invention, a screening method is provided which is based on mammalian cells, preferably human cells, in which the induction of Fra-1 expression upon incubation with the test substance can be monitored.

This screening method of the invention is based on a type of assay known in the art for identifying compounds that transcriptionally modulate the expression of a gene of interest. It may designed and carried out according to known methods, e.g. as described in WO 91/01379. It is well suited for use in a high-throughput format in order to test a great number of chemical compounds.

In a preferred aspect, the induction of Fra-1 expression upon incubation with the test compound is monitored by determining the expression of a reporter gene under the control of regulatory sequences of the fra-1 gene. The regulatory regions of the rat and murine fra-1 genes are known and easily available for the person skilled in the art (Bergers et al., 1995; Schreiber et al., 1997). They include intragenic sequences in the 5' region and sequences in the first exon and first intron of the fra-1 gene. An example for a suitable regulatory region for a reporter gene construct is a 5.5 kb fragment of the rat fra-1 gene harboring the 5 flanking sequences, exon 1 and the 5 half of intron1. Alternatively, a 1.6 kb SacI fragment containing the first 710 bp of the 5 flanking sequence, exon 1, and part of intron 1 of the fra-1 gene may be used (Bergers et al., 1995).

Preferably, the regulatory regions of the human fra-1 gene are employed. Based on the murine and rat sequences of the fra-1 gene, the human fra-1 genomic DNA can be cloned by conventional techniques, e.g. by screening human genomic libraries with rat or murine fra-1 probes, and the regulatory sequences can be obtained from the cloned gene.

Alternatively to using the fra-1 regulatory sequences, the regulatory sequence of a fra-1 target gene may be used. Fra-1 target genes, i.e. genes the expression of which is modulated by Fra-1 expression, can be identified, as described below. Target genes, the regulatory regions of which are useful to be employed in a screening assay, are those which, like fra-1, display a stimulatory effect on bone formation. In the case that the Fra-1 effect on bone formation is due to the down-regulation of the Fra-1 target gene of interest, the above-described assay can be used to identify substances which down-regulate the respective Fra-1 target gene by determining the reduced expression of the reporter gene under the control of regulatory sequences of that gene.

In a preferred embodiment, the method of the invention is carried out as follows:

In a first step, suitable test cells are selected, i.e. cells which can be easily grown in tissue culture and in which the activation of a reporter gene can be measured. In a preferred embodiment, primary osteoblasts are used as test cells. Primary osteoblasts can be obtained by methods available in the art, e.g. by the method described in Example 4. Alternatively, osteosarcoma cell lines and osteoblast-like cell lines, e.g. MC 3T3-E1 cells may be employed. Further examples for cell lines are Saos-2 (human; ATCC HTB-85), U-20S (human, ATTC HTB-96), UMR-106 or 108 (rat; ATTC CRL-1661 or ATTC CRL-1663). In principle, any other cell type may be used in which expression of Fra-1 can be induced, e.g. fibroblasts, or PC12 (rat pheochromoytoma) cells, however, the inductive effect of compounds identified in such cells has to be confirmed in osteoblasts. Thus, a screen using cells closely related to osteoblasts is preferred.

The test cells are stably transfected by conventional techniques (Sambrook, et al., 1989), with a recombinant DNA molecule containing the regulatory regions of the fra-1 gene, preferably in combination with a minimal promotor, e.g. the SV40, β-globin or TK minimal promotor sequence, fused to a reporter gene according to known methods. Any reporter gene may be used whose expression product is detectable by measuring a signal proportional to its concentration and which can be detected and quantified. Preferably, a reporter gene is employed with high sensitivity in an automated assay. Examples for preferred reporter genes are the luciferase gene (De Wet, et al., 1987), the Green Fluorescent Protein GFP (Kallunki, et al., 1994), and the lacZ gene. The cells are grown in a suitable medium in microtiter assay plates and incubated with the substances to be tested. Substances which exhibit the desired effect, i.e. the induction of Fra-1 expression, are expected to upregulate reporter activity as compared to identical control cells that are incubated under the same conditions in the absence of the test substance.

For specificity control, control cells are incubated with the test substance under the same conditions as the test cells; the control cells lacking in their reporter gene construct the fra-1 regulatory elements but being otherwise identical to the test cells; substances that will be selected as drug candidates are those which cause an increase in reporter gene expression only in cells with the fra-1 construct. (In the case of using a minimal promotor sequence in the test cells, the reporter gene in the control cells is driven by the minimal promotor sequence only.)

An alternate specificity control uses cells which are identical to or different from the test cells in cell type and contain the reporter gene under the control of a transcriptional control unit different from the fra-1 regulatory element; a test substance that has shown to increase reporter gene expression in the fra-1 test cells should induce no increase in reporter gene expression in such a control cell.

In the case of applying the assay to a Fra-1 target gene which needs to be downregulated by the compound to achieve the desired therapeutic effect, this effect is reflected by reduced expression of the reporter gene upon incubation with the substance.

To optimize the assay, the test cells are incubated, in series experiments, under varying assay conditions, with a substance known to induce Fra-1 expression in cultured cells, e.g the phenolic antioxidant tert-butylhydroquinone (Yoshioka et al., 1995) and the reporter gene expression is measured.

To further evaluate substances identified in the primary screen, secondary screens may be conducted which are based on determining biological effects associated with Fra-1 overexpression. Examples of known biological effects are achorage-independent growth in vitro, invasive growth in vitro and cell motility. Assays to measure these effects are described by Bergers et al., 1995, and Kustikova et al., 1998.

In a next step, the compounds may be tested for their osteoinductive activity, i.e. their ability to accelerate osteoblast differentiation and proliferation in vitro and/or to increase bone formation in vivo by using animal models, e.g.mice.

Toxicity and therapeutic efficacy of the compounds identified as drug candidates by the method of the invention can be determined by standard pharmaceutical procedures, which include conducting cell culture and animal experiments to determine the $IC_{50}$, $LD_{50}$, the $ED_{50}$. The data obtained are used for determining the human dose range, which will also depend on the dosage form (tablets, capsules, aerosol sprays, ampules, etc.) and the administration route (oral, buccal, nasal, paterental or rectal). A pharmaceutical composition containing the compound as the active ingredient can be formulated in conventional manner using or more physiologically active carriers and excipients. Methods for making such formulations can be found in manuals, e.g. "Remington Pharmaceutical Sciences". Examples for ingredients that are useful for formulating the compounds identified according to the present invention are also found in WO 99/18193.

The osteoinductive low-molecular compounds or fra-1 DNA molecules can be used in the therapy of circumscribed or systemic bone disorders associated with reduced bone mass, as described above.

For osteoporosis, the therapeutic strategy comprises a treatment with the osteoinductive drug until normal bone mass compared to appropiate control groups is restored. Bone mass can be assessed by determining bone mineral density. Then the treatment can be switched to established regimens for the prevention of bone loss to avoid potential side effects of overshooting bone formation.

For circumscribed bone disorders, a promising therapeutic approach may be placing bone grafts at the site of the lesion and administering fra-1 DNA locally in order to enhance bone formation.

Toxicity and therapeutic efficacy of the substances identified as drug candidates by the method of the invention can be determined by standard pharmaceutical procedures, which include conducting cell culture and animal experiments to determine the $IC_{50}$, $LD_{50}$, the $ED_{50}$. The data obtained are used for determining the human dose range, which will also depend on the dosage form (tablets, capsules, aerosol sprays, ampules, etc.) and the administration route (oral, buccal, nasal, paterental or rectal). A pharmaceutical composition containing the compound as the active ingredient can be formulated in conventional manner using or more physiologically active carriers and excipients. Methods for making such formulations can be found in manuals, e.g. "Remington Pharmaceutical Sciences". Examples for ingredients that are useful for formulating the compounds identified according to the present invention are also found in WO 99/18193.

In a further embodiment, the invention relates to fra-1 DNA for therapy, in particular for the treatment of bone disorders. In this embodiment, the DNA is employed by methods known for somatic gene therapy.

"Fra-1 DNA" designates any DNA molecule encoding Fra-1 or a fragment thereof that has the ability of inducing increased bone formation upon expression in osteoblasts. The DNA may be the entire fra-1 cDNA or genomic fra-1 DNA, a fragment or a mutant thereof, preferably of human origin. To determine the effectiveness of the DNA molecule to be employed in the gene therapy approach, the candidates, e.g. the entire fra-1 cDNA and various fragments or mutants thereof, are transferred into the target cells, i.e. the osteoblasts, by viral or non-viral gene transfer methods known in the art. Examples for viral gene transfer vectors are retroviral or adenoviral vectors, into which the sequence to be tested is inserted under the control of a constiuive or inducible promotor. The thus genetically modified cells are cultured under differentiating conditions (see Example 4), and the desired biological activity is determined by monitoring the time course of differentiation and the amount of mineralized extracellular matrix formed in vitro.

For the therapy of humans, the DNA encoding the biologically active Fra-1, is delivered by viral or non-viral gene therapy application routes such that constitutive or inducible expression of Fra-1 in osteoblasts is achieved at a level to achieve sufficient Fra-1 expression and thus the desired therapeutic effect. An example for the gene therapy is the use of retroviral or adenoviral vectors, into which the fra-1 DNA molecule, under the control of a strong promotor, is inserted. To target Fra-1 expression to osteoblasts, the promoter of the osteocalcin gene can be used (Hou et al., 1999). The fra-1 DNA may be administered systemically, e.g. in the case of osteoporosis therapy, or locally, in the case of circumscribed bone defects by applying it to the site of the defect.

In a further embodiment of the invention, transgenic animals, preferably mice, are provided which constitutively express Fra-1 in osteoblasts (fra-1 transgenic animals).

These mice are obtainable by standard technology for the generation of transgenic animals, e.g. by microinjection of the fra-1 transgene containing the murine genomic fra-1 sequence, into pronuclei of one-cell embryos (Hogan, 1994).

The fra-1 transgenic mice of the invention can be used to identify target genes regulated by Fra-1 during bone formation or other biological processes. Primary cells, e.g. osteoblasts, from fra-1 transgenic and wild-type control mice are isolated and differentiated in vitro. Differences in RNA of protein levels are determined by standard methods known in the art for differential gene transcription and/or protein expression, e.g. differential display RT-PCR analysis (Liang and Pardee, 1992; Bauer, et al.,1993), DNA microarray technology (DeRisi, et al., 1997; Schena, et al., 1995; Wodicka, et al., 1997; Ramsay, 1998), subtractive hybridization (Diatchenko, et al., 1996; Hubank and Schatz, 1994), or proteome analysis (Pennington, et al., 1997; Pasquali, et al., 1997).

The present invention provides the first genetic evidence that Fra-1 is a positive regulator of bone formation in vivo. Since Fra-1 overexpression does not appear to interfere with vital physiological functions, drugs that induce Fra-1 expression or Fra-1 itself may be used in the treatment of diseases characterized by reduced bone mass or impaired bone formation, e.g. osteoporosis and impaired bone fracture healing.

EXAMPLE 1

Generation of Transgenic Mice Overexpressing Fra-1

Figure 1A:
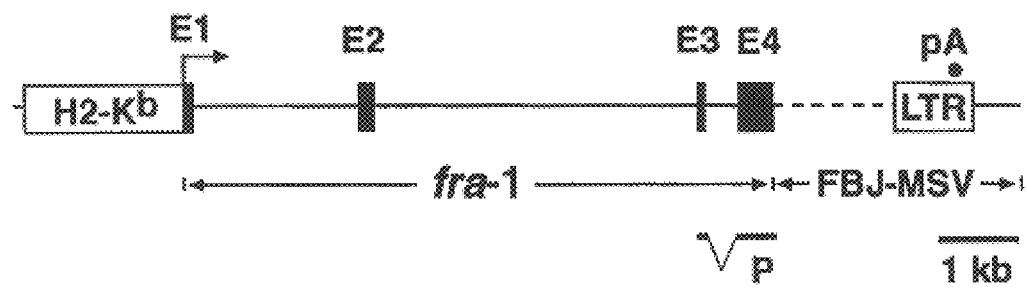
FIGS. 1A–D: Generation of fra-1 transgenic mice

To investigate the role of Fra-1 in vivo, mice overexpressing Fra-1 in a broad range of organs were generated. The transgenic vector (H2-fra-1 LTR) consisted of the murine fra-1 gene fused to the murine MHC class I H2-$K^b$ promotor (H2; Morello et al., 1986) and the 3'LTR of the FBJ-MSV virus linked to the 3' end of the fra-1 gene. The vector was constructed based on the H2-c-fosLTR vector (p128/1) described previously (Grigoriadis et al., 1993). The SalI fragment of the H2-c-fosLTR vector was replaced by murine genomic fra-1 sequences containing all 4 exons encoding the entire open reading frame (Schreiber et al., 1997). The 12 kb transgene was released by digestion with HindIII and microinjected into the pronuclei of one-cell embryos (C57BL/6× CBA F1) using standard techniques (Hogan, 1994). Transgenic progeny were identified by Southern blotting. A total of four founder males were obtained. Founder males were mated to C57/B16×CBA F1 females to establish lines. Transgenic offspring were identified by PCR analysis of tail DNA using the following primers: 5'-CGA TCA CCA AGA ACC AAT CAG-3' SEQ. ID: 1; 5'-GGG ATT AAA TGC ATG CCT AGC T-3' SEQ. ID: 2 (generating a 1.2 kb PCR product). One out of four founder males transmitted the fra-1 transgene to progeny (FIG. 1c).

To analyse fra-1 expression in transgenic mice, RNAs extracted from various organs of 3-week-old mice were investigated by RNase protection assay using a probe which detects endogenous and exogenous fra-1 transcripts. Total RNAs were isolated using Trizol reagent (GIBCO-BRL) according to manufacturer's instructions. RNAs were hybridized overnight at 60° C. with $^{32}$P-labelled anti-sense transcripts followed by digestion with RNase A and RNase T1. The protected fragments were separated on a 8% polyacrylamide/urea gel and exposed overnight. A fra-1 probe corresponding to exons 3 and 4 was used which protects a 223 bp fragment. A control S16 probe produced the 90 bp protected band. Transgenic fra-1 were detected at high levels in spleen, heart, lung, kidney and testis of transgenic mice (FIG. 1d). Lower expression levels were found in the liver, thymus, brain and long bones. Endogenous fra-1 transcripts were detected in wild-type testis. Fra-1 transgenic mice were indistiguishable from their wild-type littermates at birth; however, from 4 weeks of age on they failed to grow as rapidly as their wild-type littermates.

FIGS. 1A–D shows the generation of fra-1 transgenic mice. (a) Schematic presentation of the fra-1 transgene. P, probe used for RNase protection assay shown in d. (b) A 4-month-old transgenic mouse (Tg) and a wild-type (wt) littermate are shown. Arrow indicates the site of spinal kyphosis. (c) Southern blot analysis of fra-1 transgenic founders. The triangle marks the founder which transmitted the transgene to its progeny. (d) Fra-1 expression in various organs of 3-week-old wild-type and transgenic* mice analysed by RNase protection assay. sp, spleen; li, liver; thy, thymus; he, heart; lu, lung; te, testis; ki, kidney; br, brain.

EXAMPLE 2

Fra-1 Transgenic Mice Show Increased Bone Formation

Figure 1B:
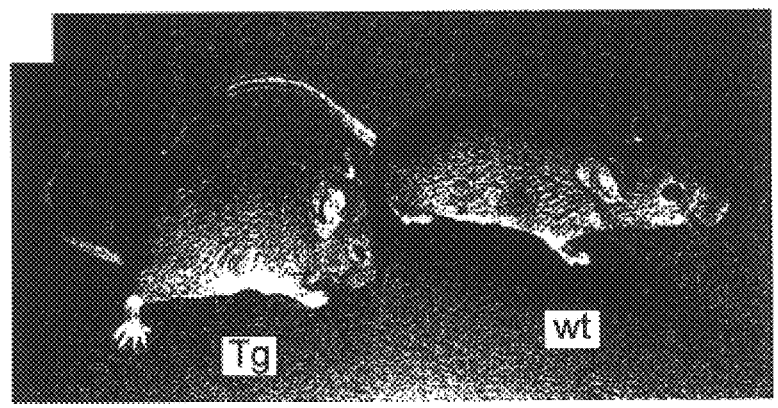
Figure 1C:
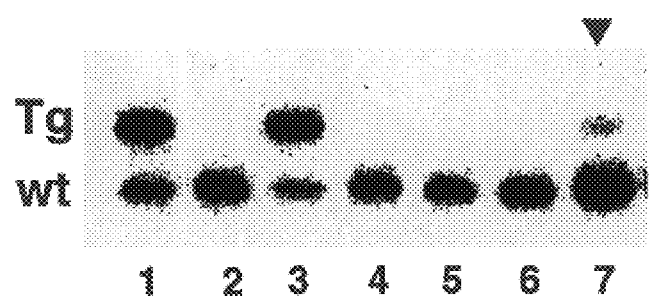
Figure 1D:
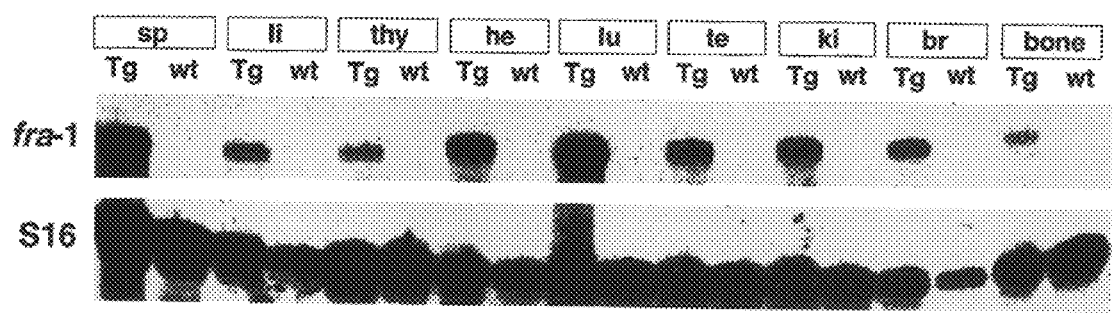
Figure 2:
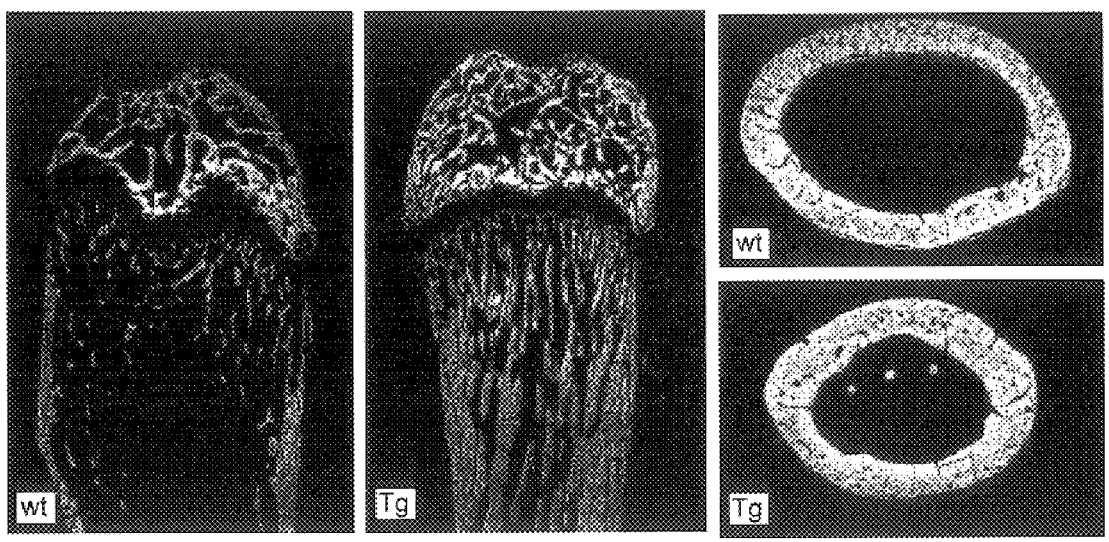
FIG. 2: Radiological analysis of fra-1 transgenic and wild-type bones

With advancing age, transgenic mice developed kyphosis of the spinal column indicative of an abnormality of the skeleton (FIG. 1b). Whole-body radiography revealed increased radiodensity of the distal and proximal ends of the long bones, vertebral bodies, ribs and the skull. Microradiographic and histological analysis of transgenic long bones revealed an increase in cortical thickness and in both the number and size of bone trabeculae, indicative of a prominent deposition of extracellular matrix (FIG. 2). In the calvaria, which also displayed increased thickness, the bone marrow spaces were obliterated by bone deposits. The surfaces of transgenic bone trabeculae were largely covered by cuboidal osteoblasts indicating functional activity. Osteoblasts frequently formed clusters suggesting an enlargement of the osteoblast compartment.

Histochemical staining for tartrate-resistant acid phosphatase (TRAP) revealed the presence of osteoclasts in both wild-type and transgenic bones. The bone matrix of wild-type and transgenic bones was homogenously mineralized and no cartilage remnants were detected. In transgenic mice radiological and histological abnormalities first became apparent at 4 weeks of age with rapid progression with increasing age. No abnormalities of skeletal patterning or tooth erruption were observed. The structure of the epiphysial growth plates, the sites of longitudinal bone growth, appeared normal. Despite the progressive deposition of bone matrix, transgenic and wild-type littermate mice displayed comparable serum levels of calcium, phosphorus and alkaline phosphatase at 10 weeks of age. However, transgenic mice developed splenomegaly and normochromic anemia suggesting that the extramedullary haematopoiesis only partially compensated for the loss of bone marrow space. In contrast, there were no significant alterations in lymyphocyte, platelet, granulocyte or monocyte numbers in the peripheral blood.

To understand the cellular mechanisms that account for the development of increased bone mass in transgenic mice, static and dynamic histomorphometric analyses were performed on the femoral metaphyses of 8-week-old mice. Trabecular bone volume was four times higher in transgenic mice compared to wild-type littermates (FIG. 3a). Histomorphometric parameters measuring the amount of newly formed bone matrix, such as osteoid volume and osteoid surface were increased in transgenic mice (FIG. 3b). Osteoblast surface was two-fold increased in transgenic bones, whereas the numbers of osteoclasts were comparable in wild-type and transgenic mice (FIGS. 3c,d). Dynamic histomorphometric parameters quantifying bone formation including mineralizing bone surface and bone formation rate were significantly higher in transgenic mice (FIGS. 3e,g). In contrast, mineral apposition rate was only slightly increased, and there was no difference in osteoid thickness (FIG. 3f). These results indicate that the increase in bone mass observed in transgenic mice is due to increased bone formation rather than to decreased bone resorption.

FIG. 2 shows a microradiography of longitudinal and transverse sections of long bones of 8-week-old wild-type and transgenic mice. In transgenic femora, the number and size of mineralized bone trabeculae (white) in the metaphysis and the thickness of the mid-diaphyseal cortex are increased.

Figure 3:
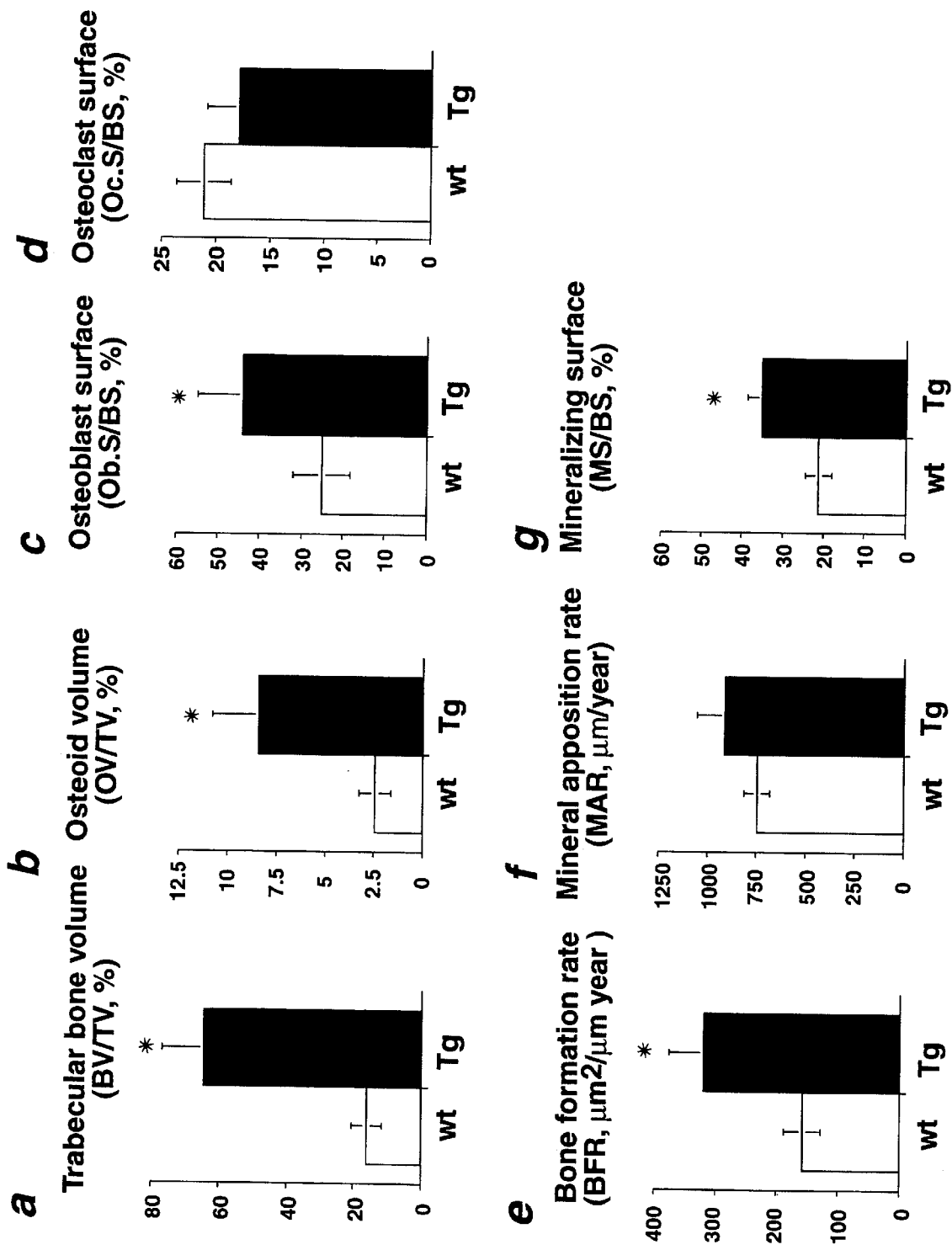
FIG. 3: Histomorphometrical analysis

FIG. 3 shows the results of the histomorphometrical analysis. Histomorphometrical analyses were performed on femora of 8-week-old transgenic (n=8) and wild-type (n=6) mice after fluorochrome-labeling with tetracyclin (25 mg/kg body weight) and calcein (25 mg/kg body weight) 10 and 7 days prior to sacrifices, respectively. Femora were fixed in 7.5% formaldehyde/75% ethanol overnight and embedded undecalcified in methylmethacrylate.

Histomorphometrical measurements were performed on Paragon-stained ground sections (50 μm) or TRAP-stained paraffin-sections (5 μm) using a Merz grid (Graticules) with 36 test points at a ×200 magnification (Merz and Schenk, 1970). Parameters for the trabecular bone were measured in an area 1.1 mm long from 0.5 mm proximal of the growth plate at the distal metaphysis of the femur. Histomorphometric parameters follow the recommended nomenclature (Parfitt et al., 1987). Student's t test was used to test for statistical significance of differences. Data are expressed as means and standard errors. BV, bone volume; TV, tissue volume; BS, bone surface. (*) Statistically significant difference between wild-type and transgenic groups; $p<0.01$ by Student's t test.

EXAMPLE 3

Figure 4A:
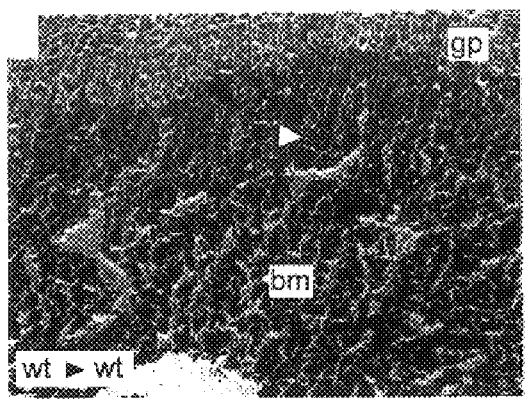
FIG. 4: Bone development in grafted wild-type and fra-1 transgenic femora
Figure 4B:
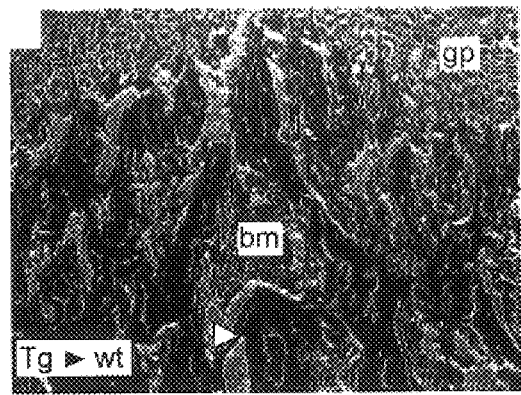
Figure 4C:
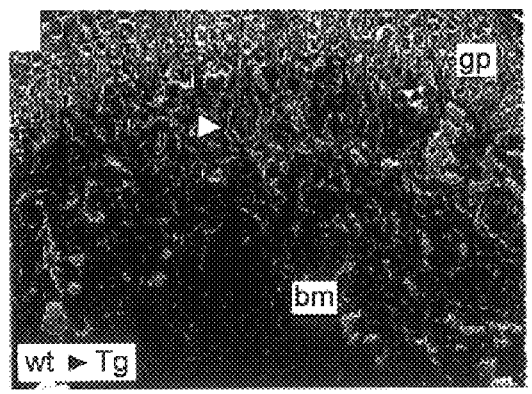
Figure 4D:
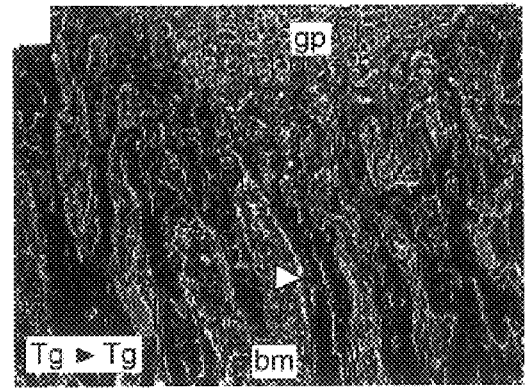

Increased Bone Formation is Due to a Cell-autonomous Phenotype of Fra-1 Transgenic Osteoblasts To test whether the increase in bone formation was due to a phenotype intrinsic to the osteoblast lineage, a tissue recombination experiment was performed. Femora from embryonic day 13.0 to 13.5 fetuses were dissected free of surrounding tissues and transplanted under the kidney capsules of syngeneic adult mice (Kratochwil et al., 1989). At this developmental stage, fetal femora consist of a bone template formed by mesenchymal cells. In the host, the grafted femora develop into chimeric bones, in which all mesenchym-derived cell types, including osteoblasts and chondrocytes, originate from the donor, whereas all haematopoietic cells, including osteoclasts, are host-derived. Grafts were collected 6 weeks after transplantation, decalcified and analysed by histology. Both wild-type and transgenic limb rudiments had developed into long bones resembling adult femurs. Numerous wide bone trabeculae were observed in the metaphyseal zone of transgenic grafts irrespective of the genotype of the recipient, indicative of an increase in bone mass (FIGS. 4b,d). In contrast, wild-type fetal limbs transferred into transgenic or wild-type recipients displayed no histological signs of increased skeletal mass (FIGS. 4a,c).

FIG. 4 shows the bone development in grafted wild-type and fra-1 transgenic femora. Femur rudiments of embryonic day 13.0 to 13.5 fetuses were transplanted under the kidney capsules of adult recipients of the indicated genotype. Grafts were collected 6 weeks later and analysed by histology. bm, bone marrow; gp, growth plate; white arrowheads, bone trabecula (Trichrome stain).

To further investigate whether increased bone formation is specific to Fra-1 overexpression, wild-type primary osteoblasts, prepared as described in Example 4, were infected with a retroviral vector driving the constitutive expression of Fra-1 (Owens et al., 1999). Upon culturing under differentiating conditions (see Example 4), fra-1 infected osteoblasts developed more mineralized extracellular matrix compared to empty vector-infected cells indicating that increased bone formation is specific to the overexpression of Fra-1.

EXAMPLE 4

Accelerated Differentiation of Fra-1 Transgenic Osteoblasts

Figure 5A:
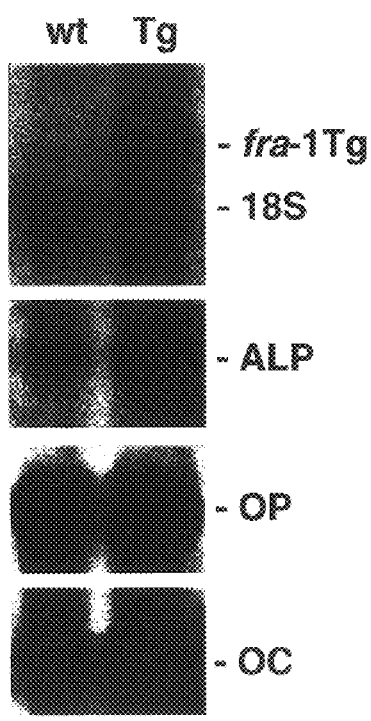
FIG. 5: Functional analysis of fra-1 transgenic osteoblasts

To study the molecular mechanisms that lead to increased bone formation, the expression of osteoblast markers were studied by Northern blot analysis in the calvariae of 4-week-old transgenic mice. Total RNAs were isolated using Trizol reagent (GIBCO-BRL) according to manufacturer's instructions and Northern blot analyses were performed as described previously (Grigoriadis et al., 1993). Transgenic fra-1 was strongly expressed in transgenic, but was absent in wild-type calvariae (FIG. 5a). The expression levels of alkaline phosphatase (ALP), osteopontin, and osteocalcin displayed a mild increase in transgenic calvaria compared to wild-type controls.

Figure 5B:
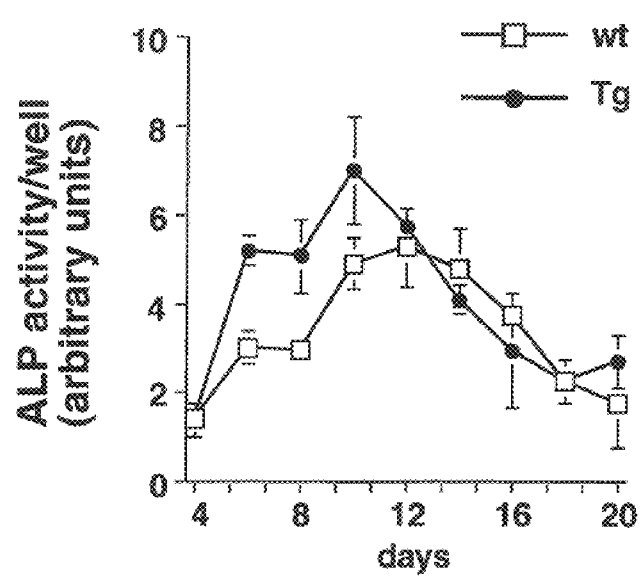

To further investigate the consequences of Fra-1 expression on osteoblasts, primary osteoblasts were prepared from the calvariae of neonatal (6–8 days old) mice and differentiated in vitro. Calvariae were sequentially digested for 10 minutes in α-MEM containing 0.1% collagenase and 0.2% dispase. Cells isolated by fractions 2 to 5 were combined as an osteoblastic cell population, expanded for 2 days in α-MEM with 10% FCS and replated at a density of $10^4$ cells per $cm^2$. After reaching confluency, medium was supplemented with 5 mM β-glycerophosphate and 100 μg/ml ascorbic acid. There was no difference in the proliferation between wild-type and transgenic osteoblasts. The time course of differentiation was followed by ALP activity and by the deposition of mineralized extracelluar matrix. For ALP activity measurement, cells were washed with PBS and sonicated in 10 mM Tris-HCl buffer (pH 8.0). ALP activity in the lysate was measured using a calorimetric assay (Sigma). Nodules of mineralized extracellular matrix were identified morphologically by alizarine red staining (Sigma). ALP activity increased faster and reached higher levels in transgenic compared to wild-type cultures (FIG. 5b). In transgenic cultures, areas of mineralized extracellular matrix monitored by alizarine red S staining were first observed at day 12, when no stained areas were present in wild-type cultures (FIG. 5b). Transgenic cultures consistently showed higher amounts of mineralized matrix at days 14, 16, and 18. Later between days 20 and 24 stained areas were of comparable size in both wild-type and transgenic cultures.

Figure 5C:
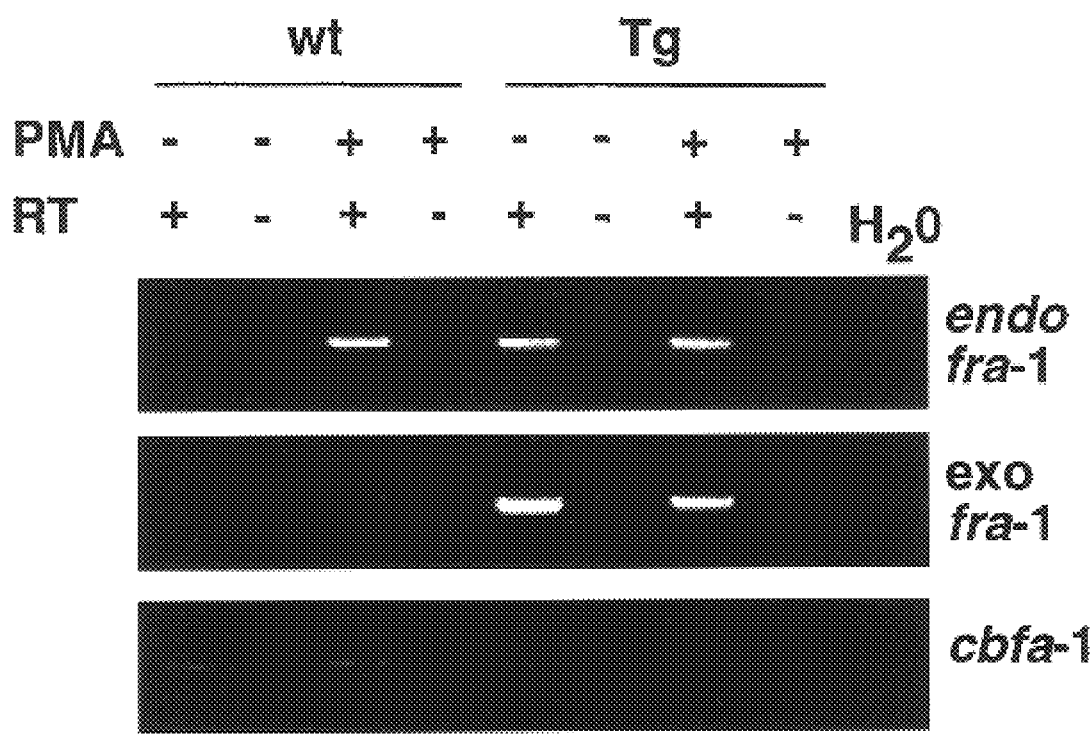

To further study expression of fra-1 and of osteoblast markers in transgenic osteoblasts, RT-PCR analysis was performed on unstimulated osteoblastic cultures 7 days after plating using primer pairs specific for endogeneous and exogenous fra-1, and for cbfa-1, type 1 collagen, and osteopontin. Total RNAs were isolated using Trizol reagent (GIBCO-BRL) according to manufacturer's instructions. For RT-PCR analysis, total RNA was reverse transcribed using SuperScript reverse transcriptase with oligo(dT) primer (GIBCO-BRL). Amplification of cDNA was performed using specific primers:

5'-GTA CCG AGA CTA CGG GGA ACC GG-3' SEQ. ID: 3 and 5'-TGG CTT GGA GTA GCA CCA GCA AGG-3' SEQ. ID: 4 for endogenous fra-1; 5'-GTA CCG AGA CTA CGG GGA ACC GG-3' SEQ. ID: 5 and 5'-CCG CTA CAG ATC CTC TTC TGA GAT G-3' SEQ. ID: 6 for exogenous fra-1; 5'-TGG AAG GGA TGA AAG GCT GC-3' SEQ. ID: 7 and 5'-TGG ACG ACA CCA TTT GTG GC-3' SEQ. ID: 8 for Cbfa1; 5'-GAC CAT GAG ATT GGC AGT GAT TTG-3' SEQ. ID: 9 and 5'-TGA TGT TCC AGG CTG GCT TTG-3' SEQ. ID: 10 for Osteopontin; 5'-AAT GGT GAG ACG TGG AAA CCC GAG-3' SEQ. ID: 11 and 5'-CGA CTC CTA CAT CTT CTG AGT TTG G-3' SEQ. ID: 12 for type 1 collagen. Exogenous and endogenous fra-1 was detected in transgenic osteoblasts, irrespective of induction by phorbol myristate acetate (PMA) (FIG. 5c). In contrast, endogenous fra-1 was not expressed in wild-type osteoblasts, but was induced upon PMA stimulation. This result indicates that exogenous Fra-1 induces expression of fra-1 from the endogenous locus, suggesting that Fra-1 positively regulates its own expression in osteoblasts. The osteoblast phenotype of the transgenic and wild-type cultures was confirmed by the expression of osteoblast markers, including cbfa-1, type 1 collagen, and osteopontin (FIG. 5c).

FIGS. 5A–C shows the analysis of fra-1 transgenic osteoblasts. (a) Northern blot analysis of fra-1, alkaline phosphatase (ALP), osteopontin (OP) and osteocalcin (OC) expression in the calvariae of 4-week-old transgenic and wild-type mice. (b) Time course of ALP activity in the lysates of wild-type and transgenic osteoblast cultures. (c) Expression analysis by RT-PCR of endogenous and exogenous fra-1 transcripts in transgenic and wild-type osteoblast cultures. PMA, phorbol myristate acetate; RT, reverse transcriptase.

References

Angel, P., et al., Phorbol ester-inducible genes contain a common cis element recognized by a TPA-modulated trans-acting factor. *Cell* 49, 729–39 (1987).

Angel, P. and Karin, M., The role of Jun, Fos and the AP-1 complex in cell-proliferation and transformation. *Biochim Biophys Acta* 1072, 129–57 (1991)

Banerjee, C. et al., Runt homology domain proteins in osteoblast differentiation: AML3/CBFA1 is a major component of a bone-specific complex. *J Cell Biochem* 66, 1–8 (1997).

Battista, S., et al. Increase in AP-1 activity is a general event in thyroid cell transformation in vitro and in vivo. *Oncogene* 17, 377–85 (1998)

Bauer, D., Muller, H., Reich, J., Riedel, H., Ahrenkiel, V., Warthoe, P., and Strauss, M., *Nucleic Acids Res.* 21, 4272–4280, (1993)

Bergers, G., Graninger, P., Braselmann, S., Wrighton, C. and Busslinger, M., Transcriptional activation of the Fra-1 gene by AP-1 is mediated by regulatory sequences in the first intron. *Mol Cell Biol* 15, 3748–58 (1995).

Candeliere, G. A., Prud'homme, J. and St-Arnaud, R., Differential stimulation of fos and jun family members by calcitriol in osteoblastic cells. *Mol Endocrinol* 5, 1780–8 (1991).

Caricasole, A. and Ward, A., Transactivation of mouse insulin-like growth factor II (IGF-II) gene promoters by the AP-1 complex. *Nucleic Acids Res* 21, 1873–9 (1993)

Clohisy, J. C., Scott, D. K., Brakenhoff, K. D., Quinn, C. O. and Partridge, N. C., Parathyroid hormone induces c-fos and c-jun messenger RNA in rat osteoblastic cells. *Mol Endocrinol* 6, 1834–42 (1992)

Cohen, D. R. and Curran, T., Fra-1: a serum-inducible, cellular immediate-early gene that encodes a fos-related antigen. *Mol Cell Biol* 8, 2063–9 (1988).

Cohen, D. R., Ferreira, P. C., Gentz, R., Franza, B. R., Jr. and Curran, T., The product of a fos-related gene, Fra-1, binds cooperatively to the AP-1 site with Jun: transcription factor AP-1 is comprised of multiple protein complexes. *Genes Dev* 3, 173–84 (1989)

Cohen, D. R., Vandermark, S. E., McGovern, J. D. and Bradley, M. P., Transcriptional regulation in the testis: a role for transcription factor AP-1 complexes at various stages of spermatogenesis. *Oncogene* 8, 443–55 (1993)

DeRisi, et al., *Science*, 278, 680 (1997)

De Wet, J. R., et al., *Mol. Cell. Biol.* 7, 725–737(1987)

Diatchenko, L., Lau, Y. F., Campbell, A. P., Chenchik, A., Moquadam, F., Huang, B., Lukyanov, S., Lukyonov, K., Gurskaya, N., Sverdlov, E. D., and Siebert, P. D., *Proc. Natl. Acad. Sci. USA* 93, 6025–6030, (1996).

Dony, C. and Gruss, P., Proto-oncogene c-fos expression in growth regions of fetal bone and mesodermal web tissue. *Nature* 328, 711–4 (1987).

Ducy, P. et al., Increased bone formation in osteocalcin-deficient mice. *Nature* 382, 448–52 (1996)

Ducy, P., Zhang, R., Geoffroy, V., Ridall, A. L. and Karsenty, G., Osf2/Cbfa1: a transcriptional activator of osteoblast differentiation. *Cell* 89, 747–54 (1997)

Ducy, P. et al., A Cbfa1-dependent genetic pathway controls bone formation beyond embryonic development. *Genes Dev* 13, 1025–36 (1999)

Filvaroff, E. and Derynck, R., Bone remodelling: a signalling system for osteoclast regulation. *Curr Biol* 8, R679–82 (1998).

Gandarillas, A. and Watt, F. M., Changes in expression of members of the fos and jun families and myc network during terminal differentiation of human keratinocytes. *Oncogene* 11, 1403–7 (1995).

Grigoriadis, A. E., Schellander, K., Wang, Z. Q. and Wagner, E. F., Osteoblasts are target cells for transformation in c-fos transgenic mice. *J Cell Biol* 122, 685–701 (1993)

Grigoriadis, A. E., et al., c-Fos: a key regulator of osteoclast-macrophage lineage determination and bone remodeling. *Science* 266, 443–8 (1994).

Guo, X., Zhang, Y. P., Mitchell, D. A., Denhardt, D. T. and Chambers, A. F., Identification of a ras-activated enhancer in the mouse osteopontin promoter and its interaction with a putative ETS-related transcription factor whose activity correlates with the metastatic potential of the cell. *Mol Cell Biol* 15, 476–87 (1995)

Hogan, B., et al., Manipulating the Mouse Embryo, A Laboratory Manual, Second Edition, *Cold Spring Harbor Laboratory Press* (1994)

Hou, Z., et al., Proc. Natl Acad Sci USA, June 22; 96(13), 7294–9, (1999)

Hubank, M. and Schatz, D. G., *Nucleic Acids Res.* 22, 5640–5648, (1994)

Huo, L. and Rothstein, T. L., Isolation and characterization of murine Fra-1: induction mediated by CD40 and surface Ig is protein kinase C dependent. *J Immunol* 157, 3812–8 (1996)

Iotsova, V., et al., Osteopetrosis in mice lacking NF-kappaB1 and NF-kappaB2. *Nat Med* 3, 1285–9 (1997)

Johnson, R. S., Spiegelman, B. M. and Papaioannou, V., Pleiotropic effects of a null mutation in the c-fos proto-oncogene. *Cell* 71, 577–86 (1992).

Joyce, M. E., Roberts, A. B., Sporn, M. B. and Bolander, M. E., Transforming growth factor-beta and the initiation of chondrogenesis and osteogenesis in the rat femur. *J Cell Biol* 110, 2195–207 (1990).

Kallunki, T., et al., *Genes Dev*, December 15, 8(24), 2996–3007 (1994)

Kim, S. J., et al., Autoinduction of transforming growth factor beta 1 is mediated by the AP-1 complex. *Mol Cell Biol* 10, 1492–7 (1990)

Koe, R. C., et al., Parathyroid hormone versus phorbol ester stimulation of activator protein-1 gene family members in rat osteosarcoma cells. *Calcif Tissue Int* 61, 52–8 (1997)

Komori, T., et al., Targeted disruption of Cbfa1 results in a complete lack of bone formation owing to maturational arrest of osteoblasts. *Cell* 89, 755–64 (1997).

Kong, Y. Y., et al., OPGL is a key regulator of osteoclastogenesis, lymphocyte development and lymph-node organogenesis. *Nature* 397, 315–23 (1999).

Kratochwil, K., et al., Retrovirus-induced insertional mutation in Movl3 mice affects collagen I expression in a tissue-specific manner. *Cell* 57, 807–16 (1989)

Kustikova, O., et al., *Mol Cell Biol*, December; 18(12), 7095–105, (1998)

Liang, P. and Pardee, A. B., *Science* 257, 967–971 (1992).

Machwate, M., Jullienne, A., Moukhtar, M., Lomri, A. and Marie, P. J., c-fos protooncogene is involved in the mitogenic effect of transforming growth factor-beta in osteoblastic cells. *Mol Endocrinol* 9, 187–98 (1995).

McCabe, L. R., Kockx, M., Lian, J., Stein, J. and Stein, G., Selective expression of fos- and jun-related genes during osteoblast proliferation and differentiation. *Exp Cell Res* 218, 255–62 (1995).

McCabe, L. R., et al., Developmental expression and activities of specific fos and jun proteins are functionally related to osteoblast maturation: role of Fra-2 and Jun D during differentiation. *Endocrinology* 137, 4398–408 (1996)

McHenry, J. Z., Leon, A., Matthaei, K. I. and Cohen, D. R., Overexpression of fra-2 in transgenic mice perturbs normal eye development. *Oncogene* 17, 1131–40 (1998)

Mechta, F., Lallemand, D., Pfarr, C. M. and Yaniv, M., Transformation by ras modifies AP1 composition and activity. *Oncogene* 14, 837–47 (1997).

Merz, W. A. and Schenk, R. K., *Acta Anat.*; 76(1): 1–15 (1970)

Morello, D., et al., *EMBO J*, Aug;5(8): 1877–83 (1986)

Noda, M. and Camilliere, J. J., In vivo stimulation of bone formation by transforming growth factor-beta. *Endocrinology* 124, 2991–4 (1989)

Otto, F., et al., Cbfa1, a candidate gene for cleidocranial dysplasia syndrome, is essential for osteoblast differentiation and bone development. *Cell* 89, 765–71 (1997).

Owen, T. A., et al., Coordinate occupancy of AP-1 sites in the vitamin D-responsive and CCAAT box elements by Fos-Jun in the osteocalcin gene: model for phenotype suppression of transcription. *Proc Natl Acad Sci USA* 87, 9990–4 (1990).

Owens, J. M., Matsuo, K., Nicholson, G. C., Wagner, E. F. and Chambers, T. J., Fra-1 potentiates osteoclastic differentiation in osteoclast-macrophage precursor cell lines. *J Cell Physiol* 179, 170–8 (1999)

Parfitt, A. M., et al., Bone histomorphometry: standardization of nomenclature, symbols, and units. Report of the ASBMR Histomorphometry Nomenclature Committee. *J Bone Miner Res* 2, 595–610 (1987)

Pasquali, C., et al., *Electrophoresis* 18, 2573–2581 (1997)

Pendas, A. M., Balbin, M., Llano, E., Jimenez, M. G. and Lopez-Otin, C., Structural analysis and promoter characterization of the human collagenase-3 gene (MMP13). *Genomics* 40, 222–33 (1997).

Pennington, S. R., et al., *Trends Cell Biol* 7, 168–173 (1997)

Ramsay, *Nature Biotechnol.*, 16, 40 (1998)

Remington's Pharmaceutical Sciences, 1980, Mack Publ. Co., Easton, Pa., Osol (ed.).

Ruther, U., Komitowski, D., Sch ubert, F. R. and Wagner, E. F., c-fos expression induces bone tumors in transgenic mice. *Oncogene* 4, 861–5 (1989).

Saftig, P., et al., Impaired osteoclastic bone resorption leads to osteopetrosis in cathepsin-K-deficient mice. *Proc Natl Acad Sci USA* 95, 13453–8 (1998)

Sambrook, J., Fritsch, E. F. and Maniatis, T., Molecular Cloning, *Cold Spring Harbor Laboratory Press* (2. Edition), (1989)

Sandberg, M., Vuorio, T., Hirvonen, H., Alitalo, K. and Vuorio, E., Enhanced expression of TGF-beta and c-fos mRNAs in the growth plates of developing human long bones. *Development* 102, 461–70 (1988).

Schena, M., et al., *Science* 270, 467 (1995)

Schreiber, M., et al., Structure and chromosomal assignment of the mouse Fra-1 gene, and its exclusion as a candidate gene for oc (osteosclerosis). *Oncogene* 15, 1171–8 (1997)

Schule, R., et al., Jun-Fos and receptors for vitamins A and D recognize a common response element in the human osteocalcin gene. *Cell* 61, 497–504 (1990)

Simonet, W. S., et al., Osteoprotegerin: a novel secreted protein involved in the regulation of bone density [see comments]. *Cell* 89, 309–19 (1997).

Slootweg, M. C., et al., Growth hormone induces expression of c-jun and jun B oncogenes and employs a protein kinase C signal transduction pathway for the induction of c-fos oncogene expression. *J Mol Endocrinol* 6, 179–88 (1991)

Smeyne, R. J., Curran, T. and Morgan, J. I., Temporal and spatial expression of a fos-lacz transgene in the developing nervous system. *Brain Res Mol Brain Res* 16, 158–62 (1992).

Suzuki, T., et al., Difference in transcriptional regulatory function between c-Fos and Fra-2. *Nucleic Acids Res* 19, 5537–42 (1991).

Rutberg, S. E., et al., Differentiation of mouse keratinocytes is accompanied by PKC-dependent changes in AP-1 proteins. *Oncogene* 13, 167–76 (1996)

Ryseck, R. P. and Bravo, R., c-JUN, JUN B, and JUN D differ in their binding affinities to AP-1 and CRE consensus sequences: effect of FOS proteins. *Oncogene* 6, 533–42 (1991).

Tondravi, M. M., et al., Osteopetrosis in mice lacking haematopoietic transcription factor PU.1. *Nature* 386, 81–4 (1997).

Vallone, D., et al., Neoplastic transformation of rat thyroid cells requires the junB and Fra-1 gene induction which is dependent on the HMGI-C gene product. *Embo J* 16, 5310–21 (1997)

Wang, Z. Q., et al., Bone and haematopoietic defects in mice lacking c-fos. *Nature* 360, 741–5 (1992).

Welter, J. F. and Eckert, R. L., Differential expression of the fos and jun family members c-fos, fosB, Fra-1, Fra-2, c-jun, junB and junD during human epidermal keratinocyte differentiation. *Oncogene* 11, 2681–7 (1995).

Wisdom, R. and Verma, I. M., Proto-oncogene FosB: the amino terminus encodes a regulatory function required for transformation. *Mol Cell Biol* 13, 2635–43 (1993).

Wodicka, et al., *Nature Biotechnol.*, 15, 1359 (1997)

Yoshioka, K., et al., *Proc Natl Acad Sci USA*, Vol. 92, 4972–4976, May (1995)

What is claimed is:

1. A method for identifying a substance for its ability to positively regulate bone formation comprising:
   (a) identifying a substance that upregulates the expression of Fra-1 in cells expressing murine, rat or human Fra-1 by administering a candidate substance to said cells in vitro; and
   (b) assaying for the ability of said substance to accelerate osteoblast differentiation in vitro, wherein the ability of said substance to accelerate osteoblast differentiation in vitro as compared to osteoblast differentiation without said substance is indicative of a substance which positively regulates bone formation.

2. The method of claim 1, wherein said substance that upregulates the expression of Fra-1 is identified by:
   (a) contacting said substance with mammalian cells transfected with a recombinant DNA molecule comprising a reporter gene under the control of regulatory sequences of a murine, rat or human fra-1 gene; and
   (b) assaying for the upregulation of expression of Fra-1, wherein the increased expression of said reporter gene is indicative that the substance upregulates the expression of Fra-1.

3. The method of claim 2, wherein at (a) said mammalian cells are selected from the group consisting of osteoblasts, osteosarcoma cells, MC 3T3-E1 cells, Saos-2 cells, U-2OS cells, UMR-106 cells, UMR-108 cells, fibroblasts and PC12 cells.

4. The method of claim 2, wherein at (a) said mammalian cells are human cells.

5. The method of claim 2, wherein said reporter gene is selected from the group consisting of a luciferase gene, a green fluorescent protein gene and a lacZ gene.

6. The method of claim 2, wherein said recombinant DNA molecule further comprises a minimal promoter selected from the group consisting of SV40, β-globin and TK minimal promoters.

7. The method of claim 2, wherein said fra-1 gene is of human origin.

8. The method of claim 2, wherein said fra-1 gene is of murine origin.

9. The method of claim 2, wherein said assay for the upregulation of expression of Fra-1 is an automated high-throughput assay.

10. The method of claim 1, wherein the activity of alkaline phosphatase is assayed, and wherein an increase in the alkaline phosphatase activity is indicative that the substance accelerates osteoblast differentiation in vitro.

11. The method of claim 1, wherein the deposition of mineralized extracellular matrix is assayed, and wherein an increase in the rate of mineralized extracellular matrix deposition is indicative that the substance accelerates osteoblast differentiation in vitro.

12. The method of claim 1, wherein the expression level of an osteoblast marker selected from the group consisting of alkaline phosphatase, osteopontin, osteocalcin, cbfa-1 and type 1 collagen is assayed, and wherein an increase in the expression level of said osteoblast marker is indicative that the substance accelerates osteoblast differentiation in vitro.

13. A method for identifying a substance for its ability to positively regulate bone formation comprising:

(a) identifying a substance that upregulates the expression of Fra-1 in cells expressing murine, rat or human Fra-1 by administering a candidate substance to said cells in vitro; and (b) assaying for the ability of said substance to increase bone formation in vivo in a wild-type mouse, wherein the ability of said substance to increase bone formation in said mouse as compared to a mouse without said substance is indicative of a substance which positively regulates bone formation.

14. The method of claim 13, wherein said substance that upregulates the expression of Fra-1 is identified by:

(a) contacting said substance with mammalian cells transfected with a recombinant DNA molecule comprising a reporter gene under the control of regulatory sequences of a murine, rat or human fra-1 gene; and (b) assaying for the upregulation of expression of Fra-1, wherein the increased expression of said reporter gene is indicative that the substance upregulates the expression of Fra-1.

15. The method of claim 14, wherein said mammalian cells are selected from the group consisting of osteoblasts, osteosarcoma cells, MC 3T3-E1 cells, Saos-2 cells, U-2OS cells, UMR-106 cells, UMR-108 cells, fibroblasts and PC12 cells.

16. The method of claim 14, wherein said mammalian cells are human cells.

17. The method of claim 14, wherein said reporter gene is selected from the group consisting of a luciferase gene, a green fluorescent protein gene and a lacZ gene.

18. The method of claim 14, wherein said recombinant DNA molecule further comprises a minimal promoter selected from the group consisting of SV40, β-globin and TK minimal promoters.

19. The method of claim 14, wherein said fra-1 gene is of human origin.

20. The method of claim 14, wherein said fra-1 gene is of murine origin.

21. The method of claim 13, wherein said assay for the upregulation of expression of Fra-1 is an automated high-throughput assay.

22. The method of claim 13, wherein a histomorphometric parameter selected from the group consisting of trabecular bone volume, osteoid volume, osteoid surface, osteoblast surface, mineralizing bone surface and bone formation rate is assayed, and wherein an increase in said histomorphometric parameter is indicative that the substance increases bone formation in vivo.

* * * * *